(12) United States Patent
Alva (10) Patent No.: US 12,102,456 B2
(45) Date of Patent: Oct. 1, 2024

(54) EQUIPMENT AND METHODS FOR REMOTE NEUROPSYCHOLOGICAL ASSESSMENT

(71) Applicant: United States Government as Represented by the Department of Veterans Affairs, Washington, DC (US)

(72) Inventor: Jessica Alva, Richmond, VA (US)

(73) Assignee: United States Government as Represented by the Department of Veterans Affairs, Washington, DC (US)

(\*) Notice: Subject to any disclaimer, the term of this patent is extended or adjusted under 35 U.S.C. 154(b) by 49 days.

(21) Appl. No.: 17/974,129

(22) Filed: Oct. 26, 2022

(65) Prior Publication Data

US 2023/0129574 A1 Apr. 27, 2023

Related U.S. Application Data

(60) Provisional application No. 63/272,034, filed on Oct. 26, 2021.

(51) Int. Cl.
| | | |
|---|---|---|
| *A61B 5/00* | (2006.01) |
| *A61B 5/16* | (2006.01) |
| *G16H 40/67* | (2018.01) |
| *H04L 65/1069* | (2022.01) |
| *H04N 7/18* | (2006.01) |
| *H04N 23/57* | (2023.01) |
| *H04N 23/90* | (2023.01) |
| *H04R 1/10* | (2006.01) |

(52) U.S. Cl.
CPC .......... *A61B 5/7465* (2013.01); *A61B 5/0077* (2013.01); *A61B 5/16* (2013.01); *A61B 5/4803* (2013.01); *A61B 5/7445* (2013.01); *G16H 40/67* (2018.01); *H04L 65/1069* (2013.01); *H04N 7/183* (2013.01); *H04N 23/57* (2023.01); *H04N 23/90* (2023.01); *H04R 1/1008* (2013.01); *A61B 2505/07* (2013.01); *A61B 2560/0431* (2013.01)

(58) Field of Classification Search
CPC ........... A45C 2011/003; H04M 1/0214; A61B 2560/0437; A61B 2560/0456
See application file for complete search history.

(56) References Cited

U.S. PATENT DOCUMENTS

| | | | | |
|---|---|---|---|---|
| 2011/0053652 A1* | 3/2011 | Won | .................. | H04M 1/22 345/173 |
| 2022/0206912 A1* | 6/2022 | Smith | .................. | G06F 11/2221 |

OTHER PUBLICATIONS

WEBSITE: https://www.hermtac.com/.

\* cited by examiner

*Primary Examiner* — Gerald Johnson
(74) *Attorney, Agent, or Firm* — Ballard Spahr LLP (57) ABSTRACT

Technologies are provided for remote neuropsychological assessments and other types of remote assessments (medical or otherwise).

20 Claims, 8 Drawing Sheets

EQUIPMENT AND METHODS FOR REMOTE NEUROPSYCHOLOGICAL ASSESSMENT

CROSS-REFERENCE TO RELATED APPLICATION

This application claims the benefit of and priority to U.S. Provisional Patent Application No. 63/272,034, filed Oct. 26, 2021, the content of which application is hereby incorporated by reference herein in its entirety.

BACKGROUND

Kits for home-based healthcare visits are available. Such kits allow healthcare providers to transport medical tools and/or other equipment (e.g., thermometer, pulse oximeter, and the like) to the home of a patient for a face-to-face medical evaluation. Such kits are simply carrying cases for healthcare professionals providing home-based healthcare in person.

SUMMARY

It is to be understood that both the following general description and the following detailed description are illustrative and explanatory only and are not restrictive.

Embodiments of this disclosure include computing devices, methods, and computer-program products that, individually or in combination, can provide a neuropsychological assessment at a distance from a clinician or another type of healthcare professional. Such an assessment can be referred to as a remote neuropsychological assessment.

Although telehealth appointments are offered by many different healthcare specialties, a neuropsychology assessment—e.g., an evaluation to determine whether a person has a cognitive disorder like dementia—via telehealth requires additional high-technology equipment in order to provide valid results and optimize the assessment experience. For example, strong and stable Internet connection, large monitor for patients to view tests on, two cameras for doctors to view patients' faces and papers during writing tests, and headphones to improve hearing. Since most patients do not have this equipment, home teleneuropsychology may, at best, be completed with high risk of invalid or unreliable results. This disclosure provides self-contained ready-to-use equipment that is shipped to patients, and permits completing an accurate neuropsychological assessment at a site separated from a healthcare professional. That is, the equipment described in this disclosure contains all the devices and articles necessary for a remote neuropsychological assessment that is accurate. Equipment of this disclosure can be referred to as Neuropsychological Assessment Clinic Kit (NPACK), simply for the sake of nomenclature. In some embodiments, equipment described in this disclosure can be applied in other disciplines besides neuropsychology and assessments besides neuropsychological assessments. In those embodiments, the equipment can contain all the devices and articles necessary for an assessment in a particular type of healthcare discipline. To that point, some equipment of this disclosure can be referred to as Medical Provider Assessment Clinic Kit (MPACK), simply for the sake of nomenclature. Further, some embodiments of the disclosure also can be applied to non-medical disciplines that can benefit from various types of assessments, such as vocational tests, scholastic aptitudes tests, or similar.

The site can be a dwelling of a patient or an individual in need of a neuropsychological assessment. Accordingly, the equipment described in this disclosure can permit applying neuropsychological assessments to individuals living in rural areas, who are unable to travel to a medical facility, and/or who want a convenient yet reliable way to receive healthcare.

Operation of the equipment described in this disclosure is straightforward and user-friendly, even for patients or other individuals with cognitive difficulties, little comfort using technology, and/or limited personal resources. The equipment described in this disclosure can be fully configured, and has a power supply and access point (AP) device integrated therein. The AP device provides wireless connectivity to Internet and/or other networks, without reliance on external routers, gateway devices, or other network elements. In an open position of the equipment, actuation of a few buttons or other types of actuators can establish communication with a live neuropsychologist that can apply a remote neuropsychological assessment using the equipment.

Although embodiments of this disclosure are illustrated with reference to neuropsychological assessments, the disclosure is not limited in that respect. Indeed, the principles and practical applications of this disclosure can be applied to a wide variety of medical assessments or non-medical assessments (such as vocational assessments). As such, as mentioned, some embodiments of the disclosure can be applied in other disciplines besides neuropsychology. Regardless of particular discipline, some embodiments of this disclosure can be applied to most any scenarios where providers rely on access to reliable communication with a subject remotely located and/or where providers could benefit from concurrent multiple points of view of activities performed by the subject.

Additional elements or advantages of this disclosure will be set forth in part in the description which follows, and in part will be apparent from the description, or may be learned by practice of the subject disclosure. The advantages of the subject disclosure can be attained by means of the elements and combinations particularly pointed out in the appended claims.

This summary is not intended to identify critical or essential features of the disclosure, but merely to summarize certain features and variations thereof. Other details and features will be described in the sections that follow. Further, both the foregoing general description and the following detailed description are illustrative and explanatory only and are not restrictive of the embodiments of this disclosure.

BRIEF DESCRIPTION OF THE DRAWINGS

The annexed drawings are an integral part of the disclosure and are incorporated into the subject specification. The drawings illustrate example embodiments of the disclosure and, in conjunction with the description and claims, serve to explain at least in part various principles, elements, or aspects of the disclosure. Embodiments of the disclosure are described more fully below with reference to the annexed drawings. However, various elements of the disclosure can be implemented in many different forms and should not be construed as limited to the implementations set forth herein. Like numbers refer to like elements throughout.

DETAILED DESCRIPTION

The disclosure recognizes and addresses, amongst other technical challenges, the lack of neuropsychological assessments implemented at a location that is separate from the location of a clinician applying the assessment. Geriatric patients with cognitive decline face multiple challenges in obtaining neuropsychological assessments. Amongst those challenges are impractical travel distance from a rural area, driving safety risks, limited alternative transportation, and burden associated with parking at a medical facility and navigating that facility. Those challenges are greatly magnified by situations outside the control of a patient, such as increased vulnerability to severe illness and fatality from a pandemic. While the feasibility and validity of teleneuropsychological assessment are research-supported, the majority of geriatric patients lack access to technology necessary for that modality of mobile health. Thus, many geriatric patients in need of neuropsychological assessment are underserved, resulting in undetected cognitive impairment, delays in treatment, suboptimal caregiver support/education, and unaddressed safety risks.

Further, existing home-based teleneuropsychology models rely on patients' technological literacy and their personal equipment, which oftentimes is inadequate for testing evaluations. Thus, those models tend to exclude patients with limited technological familiarity and/or comfort.

Embodiments of this disclosure permit timely provision of neuropsychological assessments. As a result, embodiments of this disclosure can significantly improve health and safety outcomes for geriatric patients with multiple barriers limiting access to in-person healthcare. By eliminating face-to-face contact required for a neuropsychological assessment, embodiments of this disclosure also can reduce potential risk of contracting an infectious disease (e.g., a SARS-Cov-2 infection) for individuals in vulnerable populations (such as geriatric Veterans) and clinicians treating those individuals.

Embodiments of this disclosure can expand access to neuropsychological assessment for other populations with high travel and access burden (e.g., rural patients, patients with spinal cord injury, full-time workers, and so forth). Embodiments of the disclosure also can yield cost savings for medical facilities.

Further, embodiments of this disclosure are not limited to remote neuropsychological assessment. Indeed, the principles of practical applications of the embodiments of this disclosure can be directed to other patient populations and providers whose clinical care requires greater patient observation than what a telephone or tablet computer with a single camera alone can provide. For instance, embodiments of this disclosure can permit physical therapists who need to view a patient's gait; occupational therapists who need to view a patient's ability to work with tools; neurologists who need to view motor abilities of a patient, and so forth.

Embodiments of this disclosure are user-friendly and self-contained, incorporating elements that permit valid and reliable in-home neuropsychological assessments. Patients or other individuals with cognitive impairment or little to no technology literacy can efficiently use the embodiments of this disclosure. Burden on a patient resulting from usage of a kit of this disclosure is rather minimal and can be limited to opening a case and pressing a few clearly labeled buttons. No additional operation of high-technology is required from the patient. Embodiments of this disclosure can integrate high-technology equipment for remote neuropsychological assessments, in addition to integrating other functional elements to satisfactorily (e.g., optimally or nearly-optimally) replicate traditional face-to-face testing.

Figure 1:
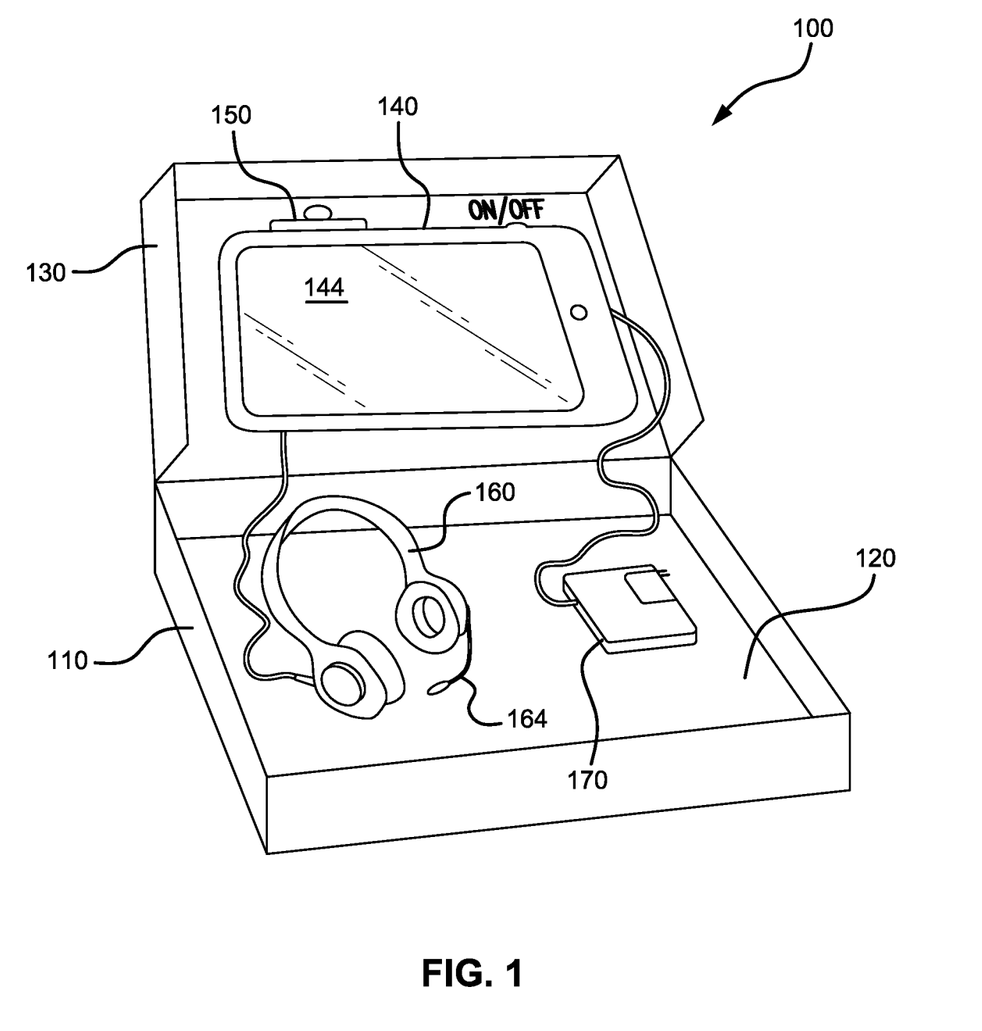
FIG. 1 illustrates a perspective view of an example of apparatus for remote neuropsychological assessments, in accordance with one or more embodiments of this disclosure.

FIG. 1 illustrates a perspective view of an example of an apparatus 100 for remote neuropsychological assessments, in accordance with one or more embodiments of this disclosure. The apparatus 100 includes a case 110 that is protective and suitable for being shipped to a location of an individual scheduled to receive a remote neuropsychological assessment. In some embodiments, the case 110 can be made from a lightweight, durable material, such as carbon fiber or another type of carbon composite. The case 110 forms a compartment 120 that can serve as a storage area for articles for neuropsychological assessment(s). The articles can include, for example, folders, papers, notebooks, pencils, or similar articles.

The case 110 has a lid 130 movably coupled to the compartment 120. The lid 130 can be assembled for placement in at least two positions relative to the compartment 120. Placement of the lid 130 in a first position of the at least two positions results in the compartment 120 being open. The first position can be referred to as an open position. Placement of the lid 130 in a second position of the at least two positions results in the compartment 120 being reversibly closed. The second position can be referred to as a closed position.

The apparatus 100 also includes a computing device 140 that can be affixed to an interior surface of the lid 130. The computing device 140 can be affixed such that the computing device 140 remains securely mounted and locked, avoiding undesired movement.

The computing device 140 can include a radio module and/or other circuitry that permits establishing a wireless connection with a second computing device (not depicted in FIG. 1) remotely located relative to the computing device 140. The wireless connection can be established via a cellular wireless network or a satellite-based wireless network, for example. The wireless connection permits the wireless exchange of data and/or signaling among the computing device 140 and the second computing device. As such, the computing device 140 is configured to establish a live call session with the second computing device. The computing device 140 can hand over control of the operation of the computing device to the second computing device after establishing the live call session. The second computing device can be operated by a healthcare provider (e.g., a clinician) and can remotely control the operation of the computing device 140. Accordingly, the live call session can eliminate reliance on patients' familiarity/comfort with technological equipment.

Figure 2:
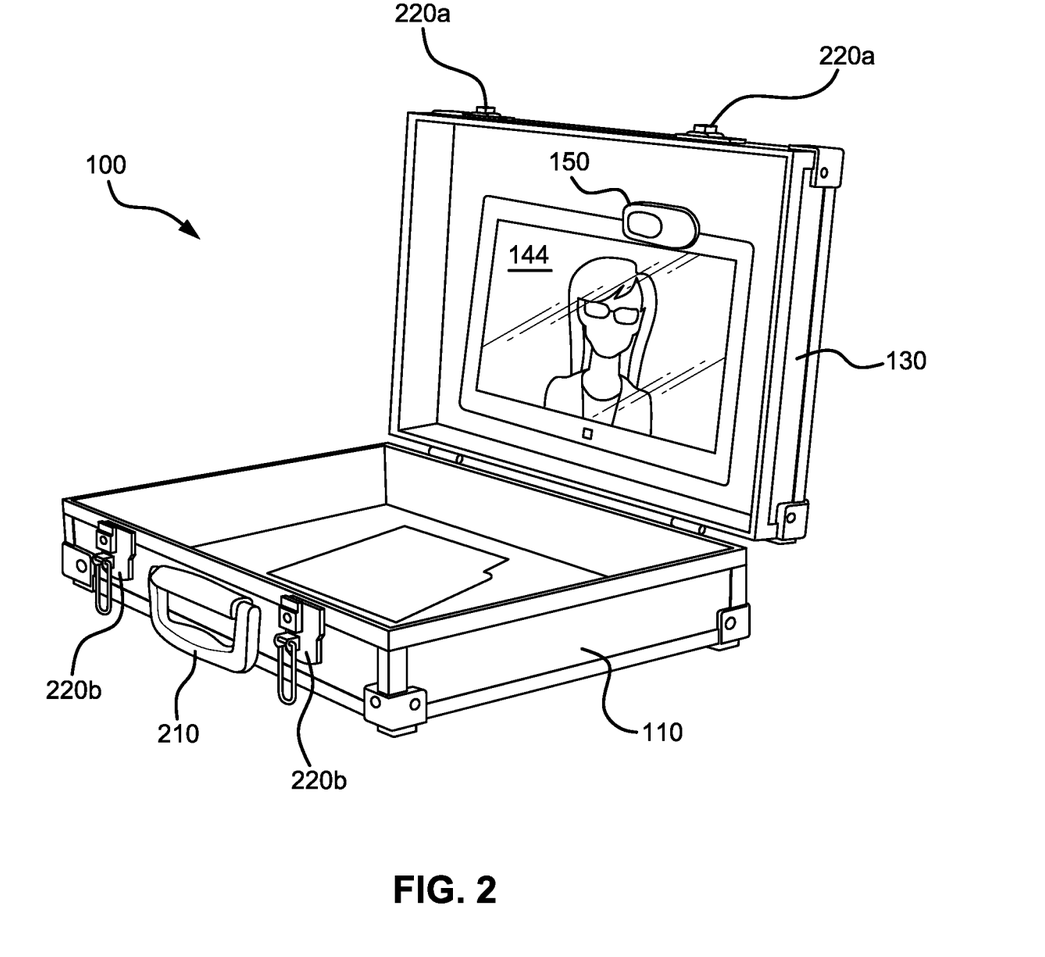
FIG. 2 illustrates a perspective view of an example of another apparatus for remote neuropsychological assessments, in accordance with one or more embodiments of this disclosure.

The computing device 140 has a display device 144 integrated therein. The display device 144 has a display surface of a size that is adequate for display of digitally content received from the second computing device. For instance, the second computing device can electronically transmit cognitive testing stimuli, such as text or other indicia, still pictures, motion pictures, animations, audio segments, or a combination thereof. In some embodiments, the display surface can be rectangular and can have a size that is equal to or greater than 10 inches measured along a diagonal of the display layer. Simply as an illustration, FIG. 2 illustrates an image of a clinician displayed at the display device 144. That image can be part of a video stream pertaining to a remote neuropsychological assessment.

Although in some embodiments the computing device 140 can have a camera device (not depicted) integrated therein, the apparatus 100 also can include a camera device 150, such as a webcam. The camera device that can be integrated into the computing device 140 can serve as an internal camera device, the camera device 150 severs as an external, secondary camera device. In operation (e.g., during a neuropsychological assessment), the internal camera device and the external, secondary camera device can be powered on at the same time, thereby allowing a remote provider to have access to multiple points of view of a subject and surrounding space. For instance, by utilizing both camera devices, the remote provider can simultaneously view the patient's face and their writing surface.

The camera device 150 can be affixed to an interior surface of the lid 130 and can be functionally coupled to the computing device. In the first position of the lid 130, where the compartment 120 is open, the camera device 150 can be oriented to have a field of view that encompasses an interior of the compartment 120 and a portion of a surface where the apparatus 100 rests. For example, the camera device 150 can be mounted and aimed to capture a writing area in front of the case 110 when open, thus providing live observation of writing/drawing tests included in a neuropsychological assessment. During the live call session, the camera device 150 can send video data to the second computing device. The video data can define a stream of images of the interior of the compartment 120 and the portion of the surface and one or more articles thereon. Thus, in some cases, camera device 150 can serve as secondary webcam.

The apparatus 100 also can include an audio output unit functionally coupled to the computing device. The audio output unit is configured to receive audio signals from the computing device 140, and further configured to convey audible audio represented by the audio signals. In addition, the apparatus 100 also can include an audio input unit functionally coupled to the computing device 140. The audio input unit is configured to send second audio signals to the computing device 140. In some embodiments, as is illustrated in FIG. 1, the audio output unit is integrated into over-the-ear headphones 160, and the audio input unit is integrated into a boom microphone 164 coupled to the over-the-ear headphones 160. Such headphones can provide satisfactory (e.g., optimal or nearly optimal) voice quality and hearing experience. In some embodiments, the headphones also can include noise-cancelling circuitry.

The apparatus 100 can further include a battery charger 170 functionally coupled to the computing device 140. The battery charger can be connected to a power grid to recharge a battery integrated into, or functionally coupled to, the computing device 140 in order to ensure that the computing device 140 and the functional elements therein can be operational. That battery can be rechargeable, and can be formed by stacking active elements (e.g., cathode, anode, separator material, and electrolyte) or a winding a multi-layered roll of such elements.

There are many embodiments of the case 110. FIG. 2 is another perspective view of the apparatus 100 illustrating an example embodiment of the case 110. As is illustrated in FIG. 2, the case 110 can include a handle 210 and one or multiple locking mechanisms to secure the case 110 in a closed position. Specifically, the case 110 can include a first locking mechanism 220a affixed to an exterior surface of the lid 130, and a second locking mechanism 220b affixed to a sidewall of the compartment. In some embodiments, the second locking mechanism 220b is configured to engage the first locking mechanism 220a to lock the apparatus 100, thereby permitting secure transportation of the apparatus 100.

Figure 3:
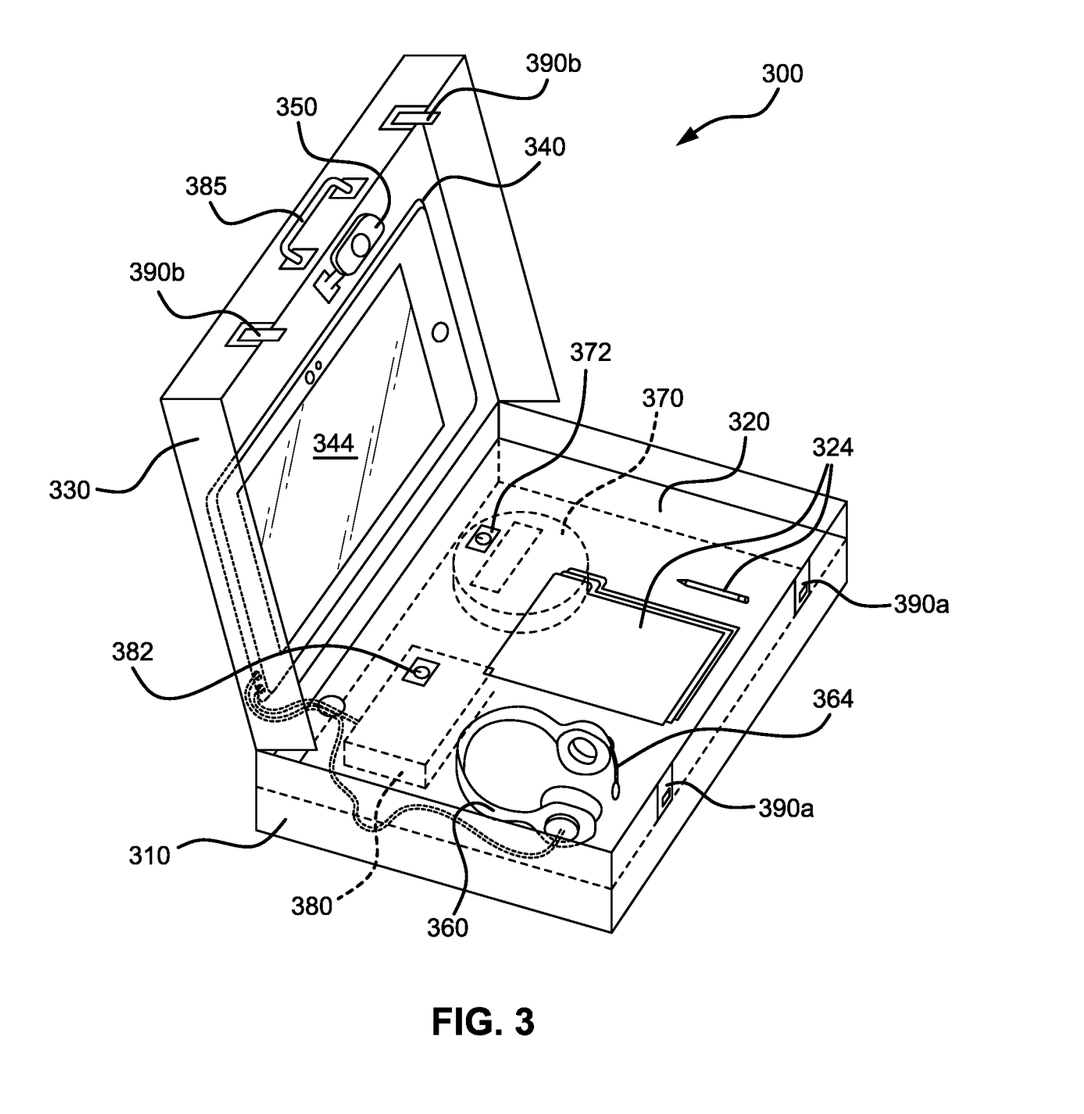
FIG. 3 illustrates a perspective view of an example of yet another apparatus for remote neuropsychological assessments, in accordance with one or more embodiments of this disclosure.

FIG. 3 illustrates a perspective view of an example of an apparatus 300 for remote neuropsychological assessments, in accordance with one or more embodiments of this disclosure. As is illustrated in FIG. 3, the apparatus 300 includes a case 310 that is protective and suitable for being shipped to a location of an individual scheduled to receive a remote neuropsychological assessment. In some embodiments, the case 310 can be made from a lightweight, durable material, such as carbon fiber or another type of carbon composite. The case 310 forms a compartment 320 that can serve as a storage area for articles 324 for neuropsychological assessment(s). The articles 324 can include, for example, folders, papers, notebooks, pencils, or similar articles.

The case 310 has a lid 330 movably coupled to the compartment 320. The lid 330 can be assembled for placement in at least two positions relative to the compartment 320. Placement of the lid 330 in a first position of the at least two positions results in the compartment 320 being open. The first position can be referred to as an open position. Placement of the lid 330 in a second position of the at least two positions results in the compartment 320 being reversibly closed. The second position can be referred to as a closed position.

The apparatus 300 also includes a computing device 340 that can be affixed to an interior surface of the lid 330. The computing device 340 can be affixed such that the computing device 340 remains securely mounted and locked, avoiding undesired movement.

The computing device 340 can include a radio module and/or other circuitry that permits establishing a wireless connection with a second computing device (not depicted in FIG. 3) remotely located relative to the computing device 340. The wireless connection can be established via a cellular wireless network or a satellite-based wireless network, for example. The wireless connection permits the wireless exchange of data and/or signaling among the computing device 340 and the second computing device. As such, the computing device 340 is configured to establish a live call session with the second computing device. The computing device 340 can hand over control of the operation of the computing device to the second computing device after establishing the live call session. The second computing device can be operated by a healthcare provider (e.g., a clinician) and can remotely control the operation of the computing device 340. Accordingly, the live call session can eliminate reliance on patients' familiarity/comfort with technological equipment.

The computing device 340 has a display device 344 integrated therein. The display device 344 has a display surface of a size that is adequate for display of digital content received from the second computing device. For instance, the second computing device can electronically transmit cognitive testing stimuli, such as text or other indicia, still pictures, motion pictures, animations, audio segments, or a combination thereof. In some embodiments, the display layer can be rectangular and can have a size that is equal to or greater than 10 inches measured along a diagonal of the display layer.

Although in some embodiments the computing device 340 can have a camera module (not depicted) integrated therein, the apparatus 300 also can include a camera device 350, such as a webcam. The camera module that can be integrated into the computing device 340 can serve as an internal camera device, the camera device 350 severs as an external, secondary camera device. The camera module is represented by a larger circle along the long side of the computing device 340. A smaller circle along that side represents a privacy light. In operation (e.g., during a neuropsychological assessment), the internal camera device and the external, secondary camera device can be powered on at the same time, thereby allowing a remote provider to have access to multiple points of view of a subject and surrounding space. For instance, by utilizing both camera devices, the remote provider can simultaneously view the patient's face and their writing surface.

The camera device 350 can affixed to an interior surface of the lid 330 and can be functionally coupled to the computing device. In the first position of the lid 330, where the compartment 320 is open, the camera device 350 can be oriented to have a field of view that encompasses an interior of the compartment 320 and a portion of a surface where the apparatus 300 rests. In other words, the camera device 350 can be mounted and aimed to capture a writing area in front of the case 310 when open, thus offering live observation of writing/drawing tests included in a neuropsychological assessment. During the live call session, the camera device 350 can send video data to the second computing device. The video data can define a stream of images of the interior of the compartment 320 and the portion of the surface and one or more articles thereon. Thus, in some cases, camera device 350 can serve as secondary webcam as is described above.

The apparatus 300 also can include an audio output unit functionally coupled to the computing device. The audio output unit is configured to receive audio signals from the computing device 340, and further configured to convey audible audio represented by the audio signals. In addition, the apparatus 300 also can include an audio input unit functionally coupled to the computing device 340. The audio input unit is configured to send second audio signals to the computing device 340. In some embodiments, as is illustrated in FIG. 3, the audio output unit is integrated into over-the-ear headphones 360, and the audio input unit is integrated into a boom microphone 364 coupled to the over-the-ear headphones 360. Such headphones can provide satisfactory (e.g., optimal or nearly optimal) voice quality and hearing experience. In some embodiments, the headphones also can include noise-cancelling circuitry.

Figure 4A:
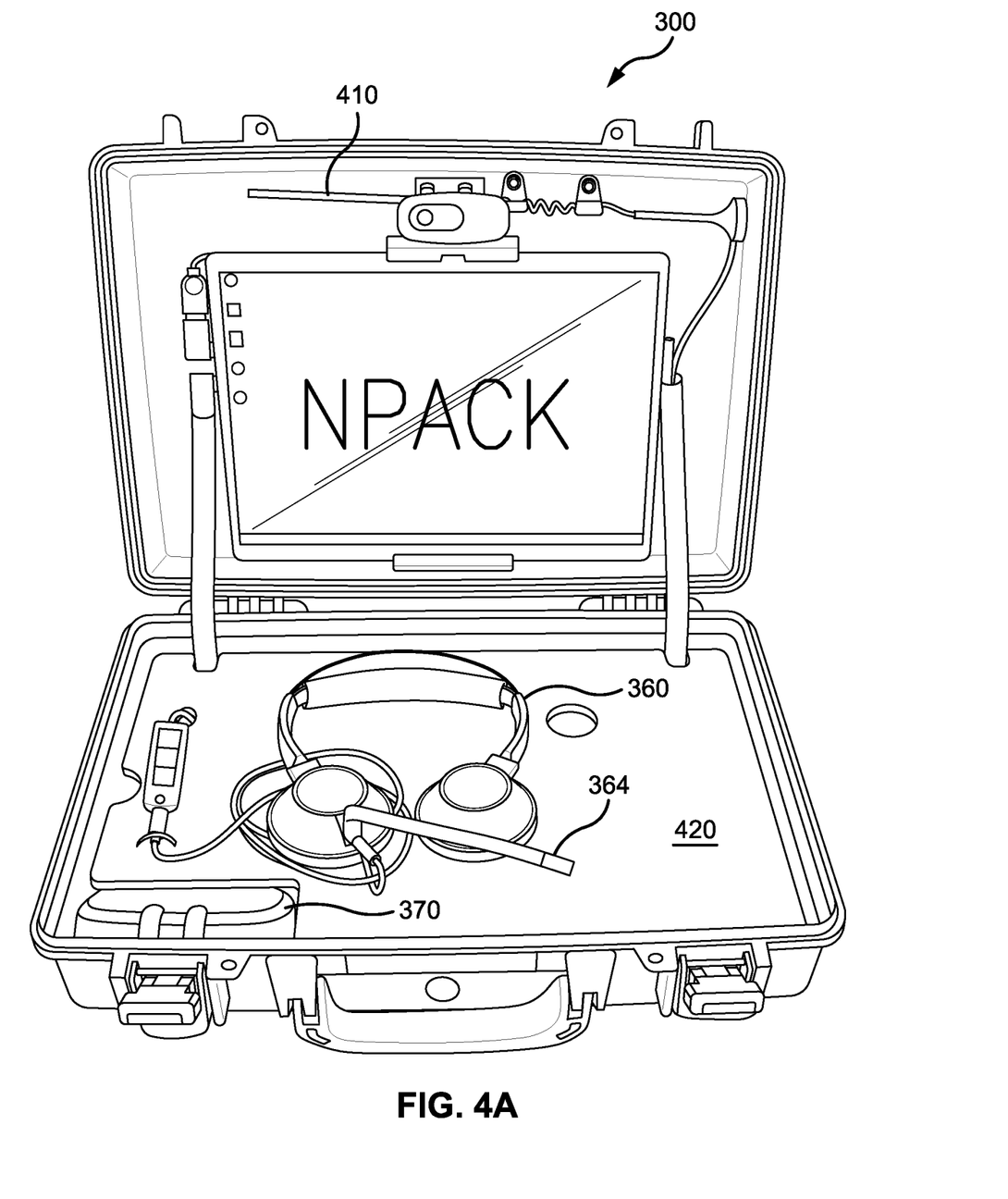
FIG. 4A illustrates a perspective view of an example of still another apparatus for remote neuropsychological assessments, in accordance with one or more embodiments of this disclosure.

The apparatus 300 also includes an access point (AP) device 370. The AP device 370 can include a radio module and/or antenna(s) that can permit the AP device 370 to emit first wireless signals according to a communication protocol that pertains to the Wi-Fi radio technology standard, and to receive second wireless signals according to that communication protocol. The disclosure, however, is not limited in that respect and, in some embodiments that AP device 370 can operate according to other wireless technologies, such as satellite-based wireless communication. In some embodiments, as is illustrated in FIG. 4A, an additional antenna 410 (such as a TS9 connector antenna) can be integrated into the apparatus 300. That additional antenna can be connected to the AP device 370 to provide even stronger internet signal.

Figure 4B:
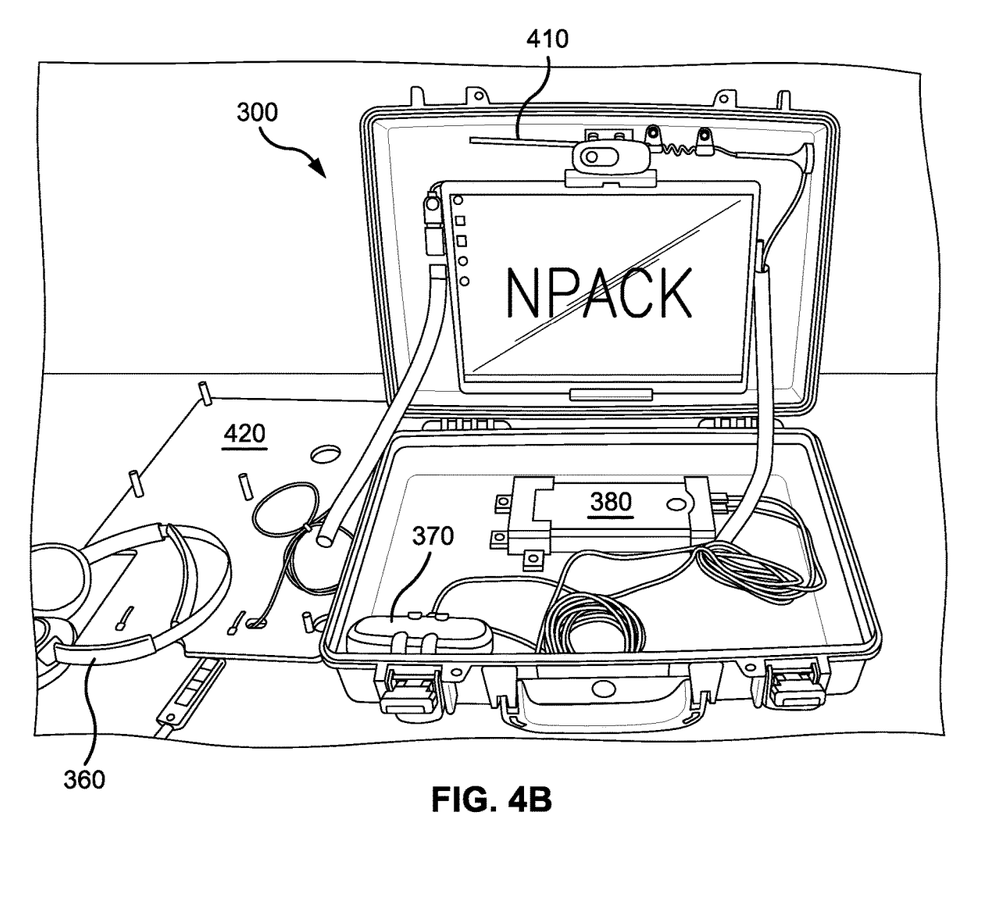
FIG. 4B illustrates a perspective view of the apparatus illustrated in FIG. 4A, where a removable tray of the apparatus has been removed, in accordance with one or more embodiments of this disclosure.

With further reference to FIG. 3, the AP device 370 can be integrated into the apparatus 300 at various positions. In one embodiment, the AP device 370 can be affixed to a base layer opposite a sidewall of the compartment 320. The base layer and the sidewall forming boundaries of a second compartment unexposed to the environment of the case 310 in the open position thereof. Because the second compartment is unexposed to the environment of the case 310 in such a position, that second compartment can serve as a hidden storage space containing most of the electronic devices integrated into the apparatus 300. In some embodiments, as is shown in FIG. 4A, that sidewall of the compartment 320 can be embodied in an acrylic tray 420 that can hide some or all of the electronic equipment integrated into the apparatus 300, within such a second compartment. The sidewall can serve as a tray that can support various articles (folders, pencils, any other clinically relevant materials, for example) that can be used for a subject as part of neuropsychological assessment or another type of assessment. That sidewall can be affixed to the base layer via screws or another type of fasteners. By being affixed to the base layer, the sidewall can limit access to the equipment present in the second compartment. In some cases, the sidewall can be removed (using a screwdriver, a wrench, or another tool, for example) to expose the equipment, as is illustrated in FIG. 4B.

The AP device 370 can have a labeled actuator 372 that is exposed to the environment of the case 310 in the open position thereof. In response to being pushed or otherwise actuated when the AP device 370 is energized, the actuator 372 causes the AP device 370 to emit first wireless signals and to receive second wireless signals in response to actuation of the labeled actuator 372. By integrating the AP device 370 (e.g., a mobile hotspot and antenna(s)) into the apparatus 300, a reliable Internet connection can be supplied and reliance on patients' home Internet service can be avoided.

Rather than relying on a battery integrated into the computing device 340, the apparatus 300 can include a power supply 380 that can energize the computing device 340, the camera device 350, the AP device 370, and in some embodiments, the headphones 360. As such, the power supply 380 can be electrically coupled to the computing device 340, the camera device 350, the AP device 370, and/or the headphones 360. The power supply 380 can be integrated into the apparatus 300 at various positions. In embodiment, the power supply 380 can be affixed to the layer onto which the AP 370 is affixed. The power supply 380 can have a labeled actuator 382 that is exposed to the environment of the case 310 in the open position thereof. In response to being pushed, the labeled actuator 382 energizes the computing device 340, the camera device 350, and/or the AP device 370, in some cases.

The power supply 380 can be embodied in, or can include, a battery. In some cases, the battery can be a lithium iodine battery (rechargeable or otherwise). In addition to the power supply 380, the apparatus 300 also can include one or more transformers (not depicted) and/or other circuitry (not depicted) to achieve a power level suitable for the operation of the various components, functional elements, and related circuitry therein, contained in the apparatus 300. In some embodiments, the apparatus 300 can include an energy conversion component, such as a solar panel, to provide additional or alternative power resources or power autonomy to the apparatus 300.

By integrating the power supply 380 into the apparatus 300, the apparatus 300 can reduce, or eliminate altogether, reliance on patients' power supply. In addition, such an integration can increase portability and can simplify use of the apparatus 300 in patients' homes.

The case 310 can include a handle 385 and one or multiple locking mechanisms to secure the case 310 in a closed position. Specifically, the case 310 can include a first locking mechanism 390a affixed to an exterior surface of the lid 330, and a second locking mechanism 390b affixed to sidewall of the compartment. In some embodiments, the second locking mechanism 390b is configured to engage the first locking mechanism 390a to lock the apparatus 300, thereby permitting secure transportation of the apparatus 300.

Although existing kits for at-home healthcare may include a carrying case and an attached tablet computer, those kits are transported and operated by a healthcare professional. More notably, the tablet computer is typically merely used to enter patient's vitals into medical record. In sharp contrast, the apparatuses of this disclosure are used by patients or other individuals in need of a neuropsychological assessment. Accordingly, a computing device included in the apparatuses of this disclosure can provide a live connection with a remote healthcare provider by, for example, executing a captive mobile application after booting the computing device. The live connection permits, at least partially, the implementation of the neuropsychological assessment. Because the apparatuses of this disclosure are self-contained, the burden on the patient to initiate and maintain the live connection for the assessment can be minimal.

Figure 5:
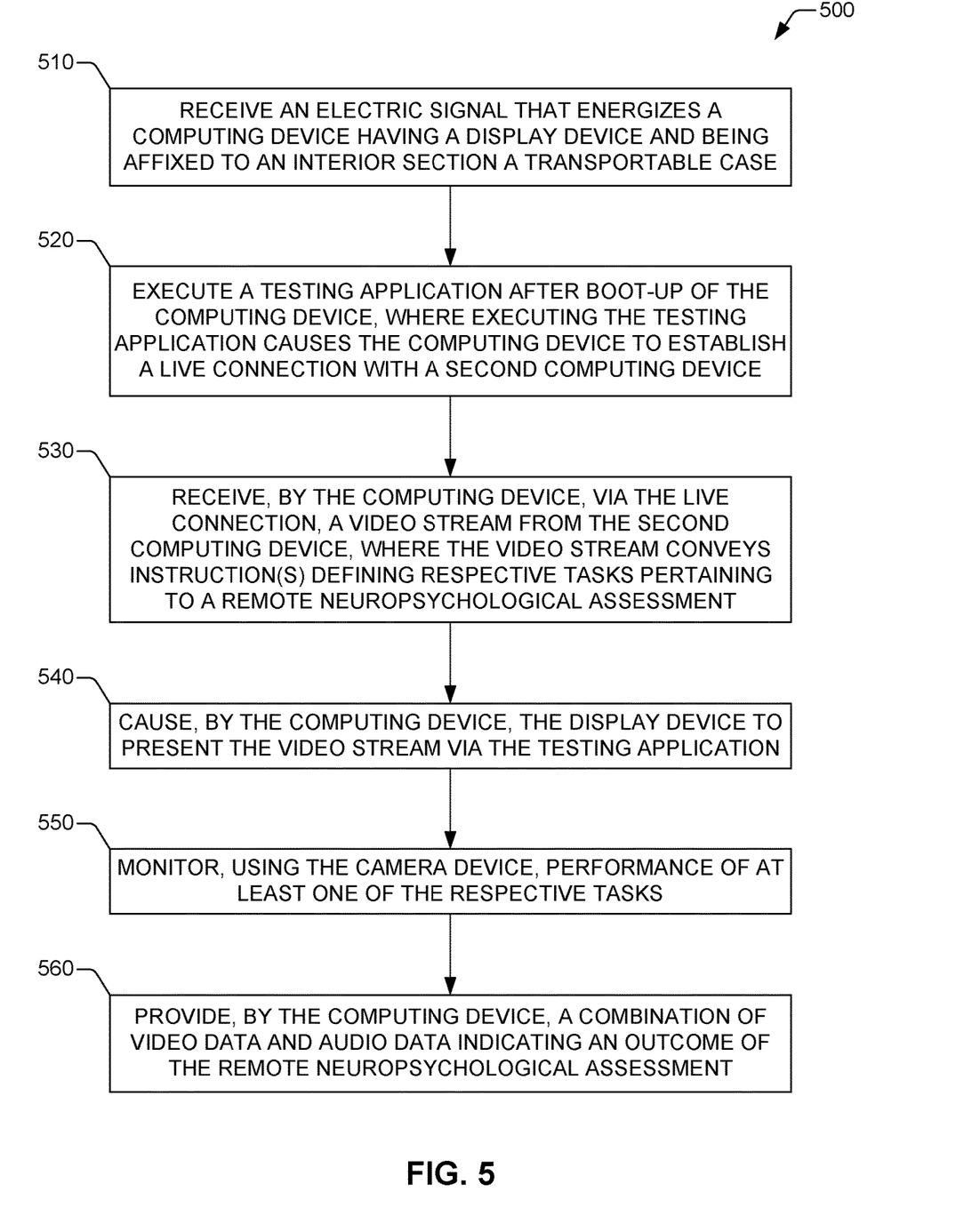
FIG. 5 illustrates an example of a method for applying a remote neuropsychological assessment, in accordance with one or more embodiments of this disclosure.

In view of the various aspects of this disclosure, an example of methods that can be implemented in accordance with embodiments of this disclosure can be more readily appreciated with reference to the flowchart in FIG. 5. For purposes of simplicity of explanation, the example method disclosed herein is presented and described as a series of blocks (with each block representing an action or an operation, for example). It is noted, however, that the methods that can be implemented in accordance with embodiments of this disclosure are not limited by the order of blocks and associated actions or operations, as some blocks may occur in different orders and/or concurrently with other blocks from those shown and described herein. In addition, not all illustrated blocks, and associated action(s), may be required to implement a method in accordance with one or more aspects of the disclosure. Further, two or more of the methods of this disclosure can be implemented in combination with each other, to accomplish one or more functionalities and/or advantages described herein. It is also noted that the various methods of this disclosure can be alternatively represented as a series of interrelated states or events, such as in a state diagram.

At least some of the methods of this disclosure can be retained on an article of manufacture, or a computer-readable non-transitory storage medium, to permit or otherwise facilitate transporting and transferring such methods to a computing device for execution, and thus implementation, by a processor of the computing device and/or for storage in a memory thereof or functionally coupled thereto. Such a computing device can be embodied in a mobile computer, such as an electronic book reader (e-reader) or other tablet computers; a smartphone; a mobile gaming console; or similar mobile device. In one aspect, one or more processors, such as processor(s) that implement one or more of the disclosed methods, can be employed to execute program instructions retained in a memory, or any computer- or machine-readable medium, to implement the one or more methods. The program instructions can provide a computer-executable or machine-executable framework to implement the methods described herein.

FIG. 5 illustrates an example of a method 500 for applying a remote neuropsychological assessment using an apparatus in accordance with one or more embodiments of the disclosure. A computing device can implement, entirely or partially, the example method 500. To that end, the computing device includes computing resources that can implement at least one of the blocks included in the example method 500. The computing resources include one or more processors or other types of processing circuitry; one or more memory devices or other types of storage circuitry; I/O interfaces; firmware; an operating system (O/S); a combination thereof; or similar resources. In some embodiments, the computing device can be embodied in the computing device 140 (FIG. 1). In other embodiments, the computing device can be embodied in the computing device 340 (FIG. 3).

At block 510, the computing device can receive an electric signal that energizes the computing device. The computing device has a display device integrated therein, and can be affixed to an interior section of a transportable case (e.g., case 110 (FIG. 1) or case 310 (FIG. 3). The electric signal can be received from a power supply integrated into the transportable case. The power supply is embodied in the power supply 380 (FIG. 3) in some cases.

At block 520, the computing device can execute a testing application after boot-up of the computing device. The testing application can be embodied in a software application having multiple software components. Each one of the multiple software components can include processor-executable program instructions or data, or a combination of both. Executing the testing application causes the computing device to establish a live connection (such as a live call session) with a second computing device remotely located relative to the computing device. To that end, computing device can use an AP device integrated into the transportable case. The AP device can be embodied in the AP device 370 (FIG. 3) in some cases. The testing application can permit applying a neuropsychological assessment or, in some embodiments, another type of assessment (medical or otherwise). In some cases, the computing device can hand over control of the operation of the computing device to the second computing device after establishing the live connection.

At block 530, the computing device can receive, via the live connection, a video stream from the second computing device. The video stream conveys one or more instructions defining respective tasks pertaining to the remote neuropsychological assessment.

At block 540, the computing device can cause the display device to present the video stream via the testing application. To that end, the computing device can execute, or can continue executing, the testing application. As a result, the testing application can direct the display device to present the video stream.

At block 550, the computing device can monitor, using a camera device functionally coupled to the computing device, performance of at least one of the respective tasks. The camera device can be embodied in the camera device 150 (FIG. 1) or the camera device 350 (FIG. 3) in some cases. The camera device can be affixed to a second interior section of the transportable case, where the second interior section can be adjacent to the first interior section. In addition, the camera device can receive an electric signal that energizes the camera device before the monitoring. An end-user, such as a patient or an individual in need of a neuropsychological assessment, can perform the at least one of the respective tasks by using a group of articles (e.g., articles stored in the transportable case.

The camera device can be oriented to have a field of view that encompasses an interior of the carrying case and a portion of a surface where the transportable case rests, the interior of the transportable case having the group of articles resting thereon. As mentioned, the articles can include, for example, folders, papers, notebooks, pencils, or similar articles. To monitor such performance, the computing device can cause the camera device to supply a video stream of a scene within the field of view. In addition, the computing device can send that video stream to the second computing device via the live connection.

At block 560, the computing device can provide at least one of video data or audio data indicating an outcome of the remote neuropsychological assessment. The video data can define a stream of images that can be presented at the display device. In one example, the stream of images can be presented by the display device 144 (see FIG. 2, for example) or the display device 344 (FIG. 3). The audio data can represent speech, for example, and can be presented by an audio output unit integrated into over-the-ear headphones (e.g., the over-the-ear headphones 160 or the over-the-ear headphones 360) included in the transportable case. Accordingly, in some cases, providing at least one of the video data or the audio data indicating an outcome of the remote neuropsychological assessment can include causing the display device 144 or the display device 344 to present the stream of images and/or causing the audio output unit to present the speech.

Figure 6:
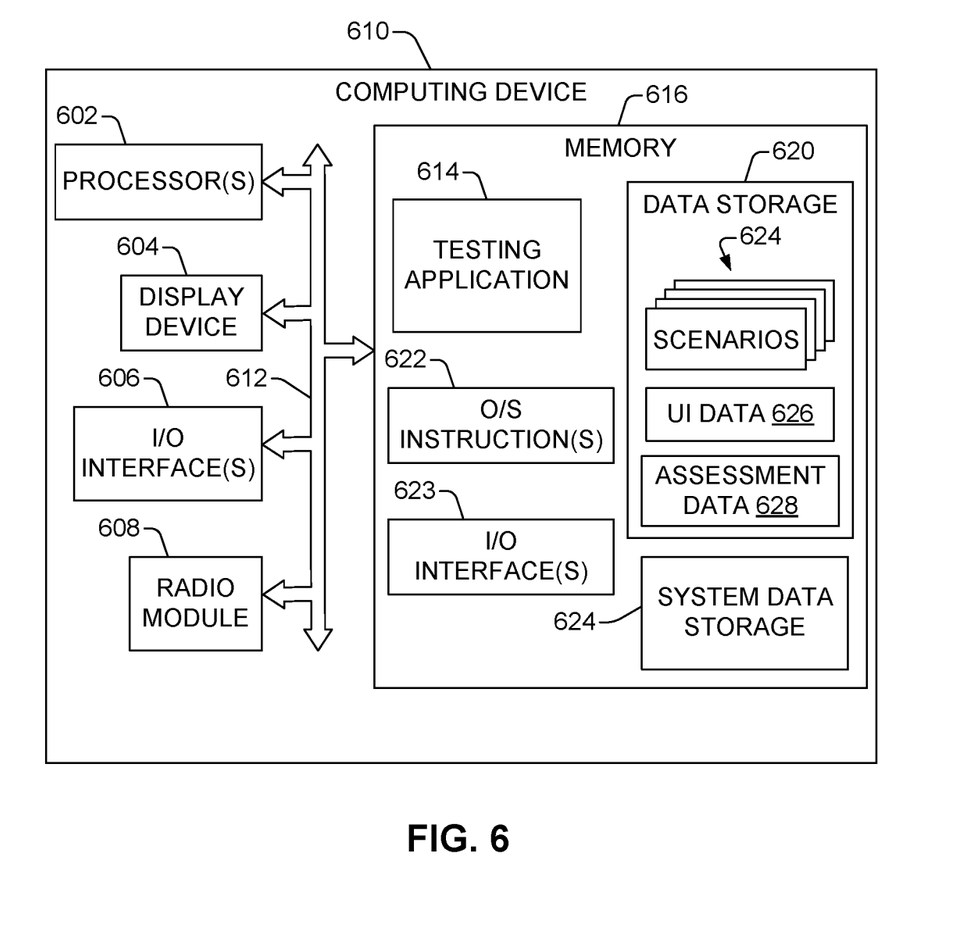
FIG. 6 illustrates an example of a computing device that can apply remote neuropsychological assessments, in accordance with one or more embodiments of the disclosure.

FIG. 6 is a block diagram of an example of a computing device 610 that can operate in accordance with one or more aspects of the disclosure. As such the computer device 610 can implement, at least partially, a remote neuropsychological assessment according to one or more embodiments of this disclosure. In some cases, the computing device 610 can embody, or can constitute, the computing device 140 (FIG. 1). In other cases, the computing device 610 can embody, or can constitute, the computing device 340 (FIG. 3). As is illustrated in FIG. 6, the computing device 610 can include one or more memory devices 616 (referred to as memory 616). The memory 616 can have processor-accessible instructions encoded thereon. The processor-accessible instructions can include, for example, program instructions that are computer readable and computer-executable.

The computing device 610 also can include one or multiple input/output (I/O) interfaces 606, a display device 604, and a radio module 608. A bus architecture 612 can functionally couple two or more of those functional elements of the computing device 610. The bus architecture 612 represents one or more of several types of bus architectures, including a memory bus or memory controller, a peripheral bus, an accelerated graphics port, and a processor or local bus using any of a variety of bus architectures. As an example, such architectures can comprise an ISA bus, an MCA bus, an EISA bus, a VESA local bus, an AGP bus, and a PCI, a PCI-Express bus, a PCMCIA bus, a USB bus, or the like.

Functionality of the computing device 610 can be configured by computer-executable instructions (e.g., program instructions or program modules) that can be executed by at least one of the one or more processors 602. Although not depicted in FIG. 6, the computer-executable instructions can be retained in the memory 616 and can constitute software and firmware of the computing device 610. A subset of the computer-executable instructions can embody the testing application 614. Such a subset can be arranged in a group of software components. A software component of the group of software components can include computer code, routines, objects, components, data structures (e.g., metadata objects, data object, control objects), a combination thereof, or the like, that can be configured (e.g., programmed) to perform a particular action or implement particular abstract data types in response to execution by the at least one processor.

Thus, the testing application 614 can be built (e.g., linked and compiled) and retained in processor-executable form within the memory 616 or another type of machine-accessible non-transitory storage media. The testing application 614 in processor-executable form, for example, can render the computing device 610 (or any other computing device that contains the testing application 614) a particular machine for remote neuropsychological assessments, among other functional purposes. The group of built software components that constitute the processor-executable version of the mobile application 614 can be accessed, individually or in a particular combination, and executed by at least one of the processor(s) 602. In response to execution, the testing application 614 can provide the functionality described herein in connection with remote neuropsychological assessments. Accordingly, execution of the group of built software components retained in the memory 616 can cause the computing device 610 to operate in accordance with aspects described herein.

Data and processor-accessible instructions associated with specific functionality of the computing device 610 can constitute software of the computing device 610 and can be retained in the memory 616. At least a portion of such data and at least a subset of those processor-accessible instructions can permit implementation of a remote neuropsychological assessment in accordance with aspects described herein. In one aspect, the processor-accessible instructions can embody any number of components (such as program instructions and/or program modules) that provide specific functionality in response to execution by at least one of the processor(s) 602. In the subject specification and annexed drawings, memory elements are illustrated as discrete blocks; however, such memory elements and related processor-accessible instructions and data can reside at various times in different storage elements (registers, files, memory addresses, etc.; not shown) in the memory 616.

The memory 616 can include data storage 620 that can comprise a variety of data, metadata, or both, associated with a remote neuropsychological assessment in accordance with aspects described herein. As is illustrated in FIG. 6, the data storage 620 can include data defining multiple training scenarios 624. The multiple training scenarios 624 can embody, or can include, the N training scenarios described above. The data storage 620 also can include UI data 626 defining various types of formatting attributes (layout, font, font size, color, etc.) for the user interfaces presented during neuropsychological assessments and other user interfaces corresponding to other functionalities of the testing application 614. The data storage 620 can further include assessment data 628 including various data identifying elements of a neuropsychological assessment, such as questions, queries, images, video segments, answers to questions or another user input, for example.

Memory 616 can be embodied in a variety of computer-readable media. Example of computer-readable media can be any available media that is accessible by a processor in a computing device (such as one processor of the processor(s) 602) and comprises, for example volatile media, non-volatile media, removable media, non-removable media, or a combination the foregoing media. As an example, computer-readable media can comprise "computer storage media," or "computer-readable storage media," and "communications media." Such storage media can be non-transitory storage media. "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, DVD or other optical storage, magnetic cassettes, magnetic tape, magnetic disk storage or other magnetic storage devices, or any other medium which can be utilized to store the desired information and which can be accessed by a computer or a processor therein or functionally coupled thereto.

Memory 616 can comprise computer-readable non-transitory storage media in the form of volatile memory, such as RAM, EEPROM, and the like, or non-volatile memory such as ROM. In one aspect, memory 616 can be partitioned into a system memory (not shown) that can contain data and/or program modules that enable essential operation and control of the computing device 610. Such program modules can be implemented (e.g., compiled and stored) in memory elements 622 (referred to as O/S instruction(s) 622) whereas such data can be system data that is retained in memory element 624 (referred to as system data storage 624). The O/S instruction(s) 622 and system data storage 624 can be immediately accessible to and/or are presently operated on by at least one processor of the processor(s) 602. The O/S instruction(s) 522 can embody an operating system for the computing device 610. Specific implementation of such O/S can depend in part on architectural complexity of the user device 610. Higher complexity affords higher-level O/Ss. Example operating systems can include iOS, Android, Windows operating system, and substantially any operating system for a mobile computing device.

Memory 616 can comprise other removable/non-removable, volatile/non-volatile computer-readable non-transitory storage media. As an example, memory 616 can include a mass storage unit (not shown) which can provide non-volatile storage of computer code, computer readable instructions, data structures, program modules, and other data for the computing device 610. A specific implementation of such mass storage unit (not shown) can depend on desired form factor of and space available for integration into the computing device 610. For suitable form factors and sizes of the computing device 610, the mass storage unit (not shown) can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), or the like.

The computing device 610 can implement, at least partially, remote neuropsychological assessments provided by the testing application 614, in accordance with aspects described herein, by executing the testing application 614. More specifically, in some embodiments, a remote neuropsychological assessments can be implemented in response to execution of software components that constitute the testing application 614 by at least one of the one or multiple processors 602.

In general, a processor of the one or multiple processors 602 can refer to any computing processing unit or processing device comprising a single-core processor, a single-core processor with software multithread execution capability, multi-core processors, multi-core processors with software multithread execution capability, multi-core processors with hardware multithread technology, parallel platforms, and parallel platforms with distributed shared memory (e.g., a cache). In addition or in the alternative, a processor of the group of one or more processors 408 can refer to an integrated circuit with dedicated functionality, such as an ASIC, a DSP, a FPGA, a CPLD, a discrete gate or transistor logic, discrete hardware components, or any combination thereof designed to perform the functions described herein. In one aspect, processors referred to herein can exploit nano-scale architectures such as, molecular and quantum-dot based transistors, switches and gates, in order to optimize space usage (e.g., improve form factor) or enhance performance of the computing devices that can implement the various aspects of the disclosure. In another aspect, the one or multiple processors 602 can be implemented as a combination of computing processing units.

The display device 604 can display the various user interfaces in connection with a remote neuropsychological assessment provided, at least in part, by the testing application 614. In some embodiments, the display device 604 can be embodied in a touch display device. Accordingly, the display device 604 can include sensing arrays, such as arrays for capacity sensing, force sensing, or resistive sensing. The display device 604 also can include circuitry for determining touch points (e.g., a pressure points or a contact points) using electric signals from the sensing arrays. The display device 604 also includes display elements, such as pixels, light emitting diodes (LEDs), substrates, and the like. The display elements can be arranged in one or multiple layers having a spatial arrangement defined by the type of display device 604; namely, frontlit display or backlit display. The display device 604 also include a solid touch layer that interfaces with an end-user.

The one or multiple I/O interfaces 606 can functionally couple (e.g., communicatively couple) the computing device 610 to another functional element (a component, a unit, server, gateway node, repository, a device, or similar). Functionality of the computing device 610 that is associated with data I/O or signaling I/O can be accomplished in response to execution, by a processor of the processor(s) 602, of at least one I/O interface retained in memory element 623. Such memory element being represented by the block labeled I/O interface(s) 623. In some embodiments, the at least one I/O interface embodies an application programming interface (API) that permit exchange of data or signaling, or both, via an I/O interface of I/O interface(s) 606. In some embodiments, the one or more I/O interfaces 606 can include at least one port that can permit connection of the computing device 610 to another other device or functional element. In one or more scenarios, the at least one port can include one or more of a parallel port (e.g., GPIB, IEEE-1284), a serial port (e.g., RS-232, universal serial bus (USB), FireWire or IEEE-1394), an Ethernet port, a V.35 port, a Small Computer System Interface (SCSI) port, or the like.

The at least one I/O interface of the one or more I/O interfaces 606 can enable delivery of output (e.g., output data or output signaling, or both) to such a device or functional element. Such output can represent an outcome or a specific action of one or more actions described herein, such as action(s) performed in the example methods described herein.

The radio module 608 can send and/or receive wireless signals from a wireless device remotely located relative to the computing device 610. The wireless signals can be sent and can be received according to a defined radio technology protocol wireless communication. The radio module 608 can include one or more antennas and processing circuitry that permit communicating wirelessly in accordance with the defined radio technology protocol. Thus, the radio module 608 can be configured to send and receive wireless signals according to one or several radio technology protocols including ZigBee™; Bluetooth™; near field communication (NFC) standards; ultrasonic communication protocols; or similar protocols. The antenna(s) and processing circuitry also can permit the radio module 608 to communicate wirelessly according to other radio technology protocols, including protocols for small-cell wireless communication and macro-cellular wireless communication. Such protocols include IEEE 802.11a; IEEE 802.1 lax; 3rd Generation Partnership Project (3GPP) Universal Mobile Telecommunication System (UMTS) or "3G;" fourth generation (4G); fifth generation (5G); 3GPP Long Term Evolution (LTE); LTE Advanced (LTE-A); wireless broadband (WiBro); and the like.

Although not shown in FIG. 6, the computing device 610 can include a battery that can power components or functional elements within the computing device 610. The battery can be rechargeable, and can be formed by stacking active elements (e.g., cathode, anode, separator material, and electrolyte) or a winding a multi-layered roll of such elements.

In addition to the battery, the computing device 610 can include one or more transformers (not depicted) and/or other circuitry (not depicted) to achieve a power level suitable for the operation of the computing device 610 and components, functional elements, and related circuitry therein. In some cases, the computing device 610 can be attached to a conventional power grid to recharge the battery and ensure that the computing device 610 and the functional elements therein can be operational. In one aspect, at least one of I/O interface(s) 606 can permit connecting to the conventional power grid. In some embodiments, the computing device 610 can include an energy conversion component, such as a solar panel, to provide additional or alternative power resources or power autonomy to the computing device 610.

Figure 7:
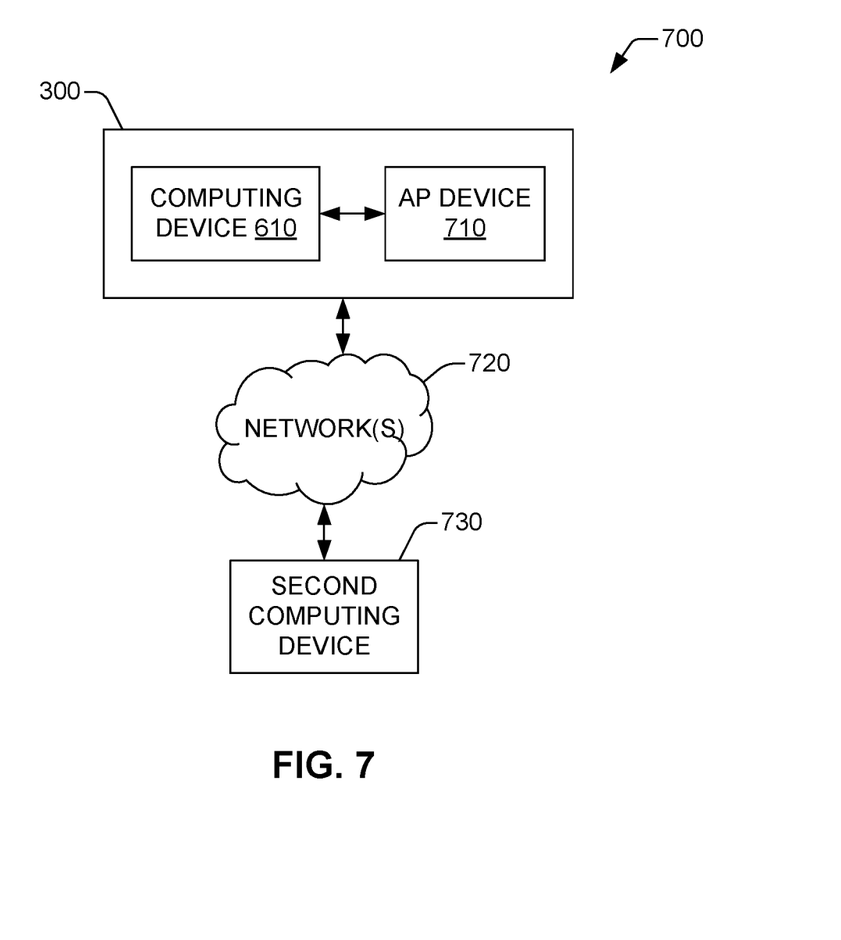
FIG. 7 illustrates an example of a computing system, in accordance with one or more embodiments of this disclosure.

FIG. 7 illustrates an example computing system 700, in accordance with one or more embodiments of this disclosure. The example computing system 700 includes the apparatus 300 which includes the computing device 610 (FIG. 6) and an access point 710. As is described herein, the computing device 610 can embody the computing device 340. The AP device 710 can be embodied in the AP device 370 (FIG. 3). It is noted that the disclosure is not limited in that respect, and in some embodiments, the computing system 700 can include the apparatus 140 containing the computing device 610 and the AP device 710.

The computing system 700 also includes one or multiple networks 720 and a second computing device 730 remotely located relative to the computing device 610. The network(s) 720 can include wireless network(s), wireline network(s), or a combination thereof, and can be have a defined coverage footprint. As is described herein, the computing device 610 can execute the testing application 614 (not shown in FIG. 7), or any other testing application described herein, to establish a live connection (such as a live call session) with the second computing device 730. To that end, computing device 610 can use the AP device 710 integrated into the apparatus 300. The AP device 710 can permit exchanging data and/or signaling between the computing device 610 and the second computing device 730. Such data and signaling can be exchanged, at least partially, via one or more of the network(s) 720. The data can include, as part of the live connection, video data or audio data, or both. As mentioned, in some cases, the computing device 610 can hand over control of the operation of the computing device 610 to the second computing device 730 after establishing the live connection.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another configuration includes from the one particular value and/or to the other particular value. When values are expressed as approximations, by use of the antecedent "about," it will be understood that the particular value forms another configuration. It will be further understood that the endpoints of each of the ranges are significant both in relation to the other endpoint, and independently of the other endpoint.

Throughout the description and claims of this specification, the words "include" and "comprise" and variations of the word, such as "including," "comprising," "includes" and "comprises," mean "including but not limited to," and are not intended to exclude other components, integers or steps. "Such as" is not used in a restrictive sense, but for explanatory purposes.

It is understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (e.g., non-transitory) having processor-executable instructions (e.g., computer software) embodied in the storage medium. Any suitable computer-readable storage medium may be utilized including hard disks, CD-ROMs, optical storage devices, magnetic storage devices, memristors, Non-Volatile Random Access Memory (NVRAM), flash memory, or a combination thereof.

Throughout this application reference is made to block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a general purpose computer, special purpose computer, or other programmable data processing apparatus to produce a machine, such that the processor-executable instructions which execute on the computer or other programmable data processing apparatus create a device for implementing the functions specified in the flowchart block or blocks.

These processor-executable instructions may also be stored in a computer-readable memory that may direct a computer or other programmable data processing apparatus to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the processor-executable instructions that execute on the computer or other programmable apparatus provide steps for implementing the functions specified in the flowchart block or blocks.

Accordingly, blocks of the block diagrams and flowcharts support combinations of devices for performing the specified functions, combinations of steps for performing the specified functions and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

This detailed description may refer to a given entity performing some action. It should be understood that this language may in some cases mean that a system (e.g., a computer) owned and/or controlled by the given entity is actually performing the action.

While specific configurations have been described, it is not intended that the scope be limited to the particular configurations set forth, as the configurations herein are intended in all respects to be possible configurations rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of configurations described in the specification. It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

What is claimed is:

1. An apparatus, comprising:
    a compartment;
    a lid movably coupled to the compartment, the lid being assembled for placement in at least two positions relative to the compartment, wherein placement of the lid in a first position of the at least two positions results in the compartment being open;
    a computing device affixed to an interior surface of the lid, the computing device having a display device and a camera device integrated therein;
    a second camera device affixed to the interior surface of the lid and functionally coupled to the computing device;
    a power supply affixed to a sidewall of the compartment and electrically coupled to the computing device, the power supply having a labeled actuator that energizes the computing device and the second camera device in response to actuation of the labeled actuator; and
    an access point (AP) device affixed to the sidewall, the AP device having a second labeled actuator that causes the AP device to emit first wireless signals and to receive second wireless signals in response to actuation of the second labeled actuator.

2. The apparatus of claim 1, further comprising,
    an audio output unit functionally coupled to the computing device, the audio output unit configured to receive audio signals from the computing device and further configured to convey audible audio represented by the audio signals; and
    an audio input unit functionally coupled to the computing device, the audio input unit configured to send second audio signals to the computing device.

3. The apparatus of claim 2, wherein the audio output unit is integrated into over-the-ear headphones, and wherein the audio input unit is integrated into a boom microphone coupled to the over-the-ear headphones.

4. The apparatus of claim 1, wherein the computing device is configured to establish a live call session with a second computing device remotely located relative to the computing device.

5. The apparatus of claim 4, wherein the computing device hands over control of operation of the computing device to the second computing device after establishing the live call session.

6. The apparatus of claim 5, wherein in the first position the second camera device is oriented to have a field of view that encompasses an interior of the compartment and a portion of a surface where the apparatus rests.

7. The apparatus of claim 6, wherein the second camera device sends video data to the second computing device, the video data defining a stream of images of the interior of the compartment and the portion of the surface and one or more articles thereon; and
    wherein the camera device sends second video data to the second computing device, the second video data defining a second stream of images of a face of a subject.

8. The apparatus of claim 1, wherein the AP device emits the first wireless signals according to a communication protocol that pertains to Wi-Fi radio technology standard, and wherein the AP device receives the second wireless signals according to the communication protocol.

9. The apparatus of claim 1, wherein placement of the lid in a second position of the at least two positions results in the compartment being reversibly closed.

10. The apparatus of claim 9, further comprising,
a first locking mechanism affixed to an exterior surface of the lid; and
a second locking mechanism affixed to a second sidewall of the compartment, the second locking mechanism being configured to engage the first locking mechanism to lock the apparatus, thereby permitting secure transportation of the apparatus.

11. The apparatus of claim 1, wherein the computing device is a tablet computer, and wherein the display device has a rectangular display surface facing an end-user, the rectangular display surface having a diagonal that is at least 10 inches long.

12. A method, comprising:
receiving, by a computing device, from a power supply, an electric signal that energizes the computing device, wherein the computing device comprises a display device and is affixed to a first interior section of a transportable case, and wherein the power supply is integrated into the transportable case;
executing a testing application by the computing device after boot-up of the computing device, the executing causes the computing device to establish a live connection with a second computing device remotely located relative to the computing device;
receiving, by the computing device, via the live connection, a video stream from the second computing device, the video stream conveying one or more instructions defining respective tasks pertaining to a remote neuropsychological assessment;
causing, by the computing device, the display device to present the video stream via the testing application; and
monitoring, using a camera device functionally coupled to the computing device, performance of at least one of the respective tasks using a group of articles stored in the transportable case, wherein the camera device is affixed to a second interior section of the transportable case.

13. The method of claim 12, further comprising providing, by the computing device, at least one of video data or audio data indicating an outcome of the remote neuropsychological assessment.

14. The method of claim 12, further comprising receiving, by the camera device, a second electric signal that energizes the camera device before the monitoring.

15. The method of claim 12, wherein the second interior section is adjacent to the first interior section, and wherein the camera device is oriented to have a field of view that encompasses an interior of the transportable case and a portion of a surface where the transportable case rests, the interior of the transportable case having the group of articles resting thereon.

16. The method of claim 15, wherein the monitoring comprises,
causing the camera device to supply a video stream of a scene within the field of view; and
sending the video stream of the scene to the second computing device via the live connection.

17. At least one computer-readable non-transitory storage medium having processor-executable instructions encoded thereon that, in response to execution, cause a computing device to:
receive, from a power supply, an electric signal that energizes the computing device, wherein the computing device comprises a display device and is affixed to a first interior section of a transportable case, and wherein the power supply is integrated into the transportable case;
execute a testing application after boot-up of the computing device, the executing causes the computing device to establish a live connection with a second computing device remotely located relative to the computing device;
receive, via the live connection, a video stream from the second computing device, the video stream conveying one or more instructions defining respective tasks pertaining to a remote neuropsychological assessment;
cause the display device to present the video stream via the testing application; and
monitor, using a camera device functionally coupled to the computing device, performance of at least one of the respective tasks using a group of articles stored in the transportable case, wherein the camera device is affixed to a second interior section of the transportable case.

18. The at least one computer-readable non-transitory storage medium of claim 17, wherein the processor-executable instructions, in response to further execution, further cause the computing device to provide at least one of video data or audio data indicating an outcome of the remote neuropsychological assessment.

19. The at least one computer-readable non-transitory storage medium of claim 17, wherein monitoring performance of the at least one of the respective tasks comprises,
causing the camera device to supply a video stream of a scene within a field of view; and
sending the video stream of the scene to the second computing device via the live connection.

20. The at least one computer-readable non-transitory storage medium of claim 17, wherein the processor-executable instructions, in response to further execution, further cause the computing device to hand over control of operation of the computing device to the second computing device after establishing the live connection.

* * * * *